United States Patent
Patton et al.

[19]

[11] Patent Number: 6,102,846

[45] Date of Patent: Aug. 15, 2000

[54] SYSTEM AND METHOD OF MANAGING A PSYCHOLOGICAL STATE OF AN INDIVIDUAL USING IMAGES

[75] Inventors: David L. Patton, Webster; John R. Fredlund, Rochester; Cecelia M. Horwitz, Penfield; Jose M. Mir, Rochester, all of N.Y.

[73] Assignee: Eastman Kodak Company, Rochester, N.Y.

[21] Appl. No.: 09/031,245

[22] Filed: Feb. 26, 1998

[51] Int. Cl.$^7$ .................................................. A61M 21/00
[52] U.S. Cl. .......................... 600/26; 600/544; 600/545
[58] Field of Search .................................. 600/509, 544, 600/545, 546, 547, 548, 26, 27; 128/898

[56] References Cited

U.S. PATENT DOCUMENTS

| | | |
|---|---|---|
| 3,855,998 | 12/1974 | Hidalgo-Briceno . |
| 4,456,347 | 6/1984 | Stahly . |
| 4,632,126 | 12/1986 | Aguilar . |
| 5,253,168 | 10/1993 | Berg . |
| 5,304,112 | 4/1994 | Mrklas et al. . |
| 5,343,871 | 9/1994 | Bittman et al. . |
| 5,403,261 | 4/1995 | Shimizu et al. . |
| 5,465,729 | 11/1995 | Bittman et al. . |
| 5,543,964 | 8/1996 | Taylor et al. . |
| 5,596,994 | 1/1997 | Bro . |
| 5,639,580 | 6/1997 | Morton . |
| 5,681,259 | 10/1997 | August ..................................... 600/27 |

OTHER PUBLICATIONS

Prevention Magazine, "Stress-Free Living", Fall 1997, pp. 56-61.

*Primary Examiner*—Linda C. M. Dvorak
*Assistant Examiner*—R. Kearney
*Attorney, Agent, or Firm*—William F. Noval

[57] ABSTRACT

A system which includes an apparatus and method of managing a psychological and physiological state of that individual involves the use of images or stimuli, the measurement of a physiological state of the individual, and the creation of a personalized preferred response profile which is specifically tailored to the individual. With the apparatus and method of the present invention, it is possible for an individual to manage and thereby lower his or her stress by viewing, for example, images which are selected based on the created personalized preferred response profile for the individual. The personalized preferred response profile is created by having the individual view, for example, a wide variety of images and creating the profile based on those images which provide a preferred response to the individual. The system supports and enhances existing biofeedback equipment.

17 Claims, 8 Drawing Sheets

FIG. 2
FIG. 2A
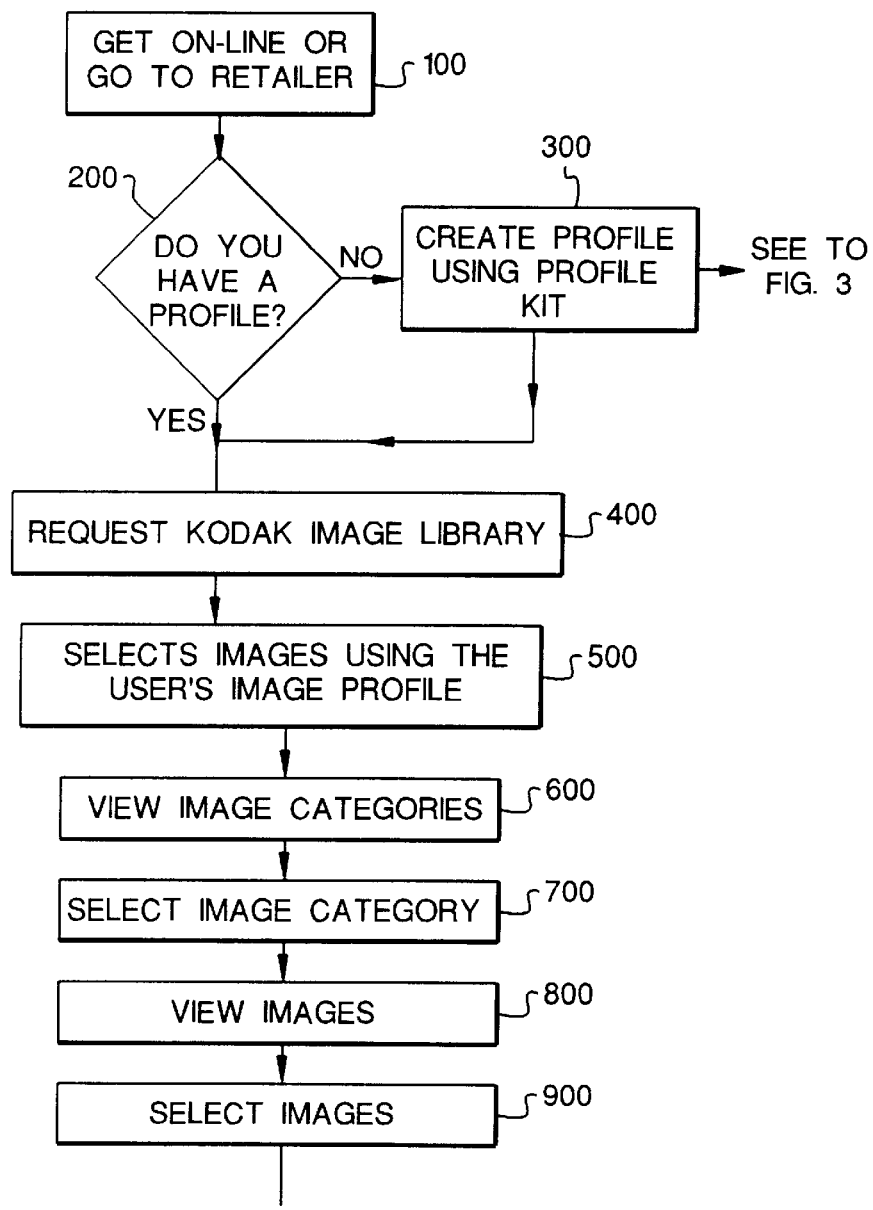

| | PRIMARY SUBJECT | SECONDARY SUBJECT | TERTIARY SUBJECT | AVERAGE LUMINANCE | DOMINANT HUE | DOMINANT HUE PREVALENCE | SECONDARY HUE | SECONDARY HUE PREVALENCE |
|---|---|---|---|---|---|---|---|---|
| 1 | MOUNTAINS | WATER | SKY | 28% | BLUE | 24% | GRAY | 8% |
| 2 | WATER | SAILBOAT | SKY | 14% | BLUE | 52% | WHITE | 12% |
| 3 | WHEATFIELD | SKY | MOUNTAINS | 24% | BROWN | 34% | BLUE | 20% |
| 4 | WATER | ROCKS | VEGETATION | 35% | GREEN | 28% | WHITE | 14% |
| 5 | SAND | SKY | WATER | 15% | BROWN | 42% | BLUE | 32% |
| 6 | VEGETATION | BRIDGE | ROCKS | | | | | |
| 7 | | | | | | | | |
| 8 | | | | | | | | |
| 9 | | | | | | | | |
| 10 | | | | | | | | |

IMAGES / ATTRIBUTES

FIG. 6

SYSTEM AND METHOD OF MANAGING A PSYCHOLOGICAL STATE OF AN INDIVIDUAL USING IMAGES

FIELD OF THE INVENTION

The present invention relates to the field of measuring and helping individuals manage their stress, by utilizing images or stimuli along with or as part of a biofeedback mechanism to assist individuals in managing their stress.

BACKGROUND OF THE INVENTION

The measurement and management of a psychological and physiological state, such as the stress, of an individual is a component of a health management program. In order to manage stress which has both a psychological and physiological component, it is useful to measure a physiological state of an individual by measuring a galvanic skin response, a temperature of the extremities of the individual such as the fingers and toes, electromyographic (EMG) signals, electroencephalograph (EEG) signals, heart rate, blood pressure, etc., to determine the stress level or level of anxiety of the individual. One can also measure the dilation of the pupil of the eye of an individual to determine his or her stress level. The results of these measurements are converted into signals and fed back to the individual as an indication of the individual's level of stress. The level of stress of an individual can be determined from a predetermined base level, then converted into sound, light, heat, vibration or images and fed back to the individual. The individual in employing stress reducing techniques uses the sound, light or images to reduce his or her stress. Changes due to physical measures are shown to the individual by a biofeedback device by changing the sound, heat, vibration, light, or images. In the case of images, the initial state may show the image out of focus, and as the stress level goes down, the images become more defined. In U.S. Pat. No. 5,465,729, measurements of electro-physiological quantities are used to control a presentation to a subject of a series of prestored audio-visual sequences. In this reference, the image does not have to provide feedback and can be used to achieve a relaxed state.

U.S. Pat. No. 3,855,998 shows an entertainment device that includes sensing means connected to the user. In this reference, the sensing means can, for example, sense a galvanic skin response of the user, and according to the given measured state of the user, the device provides a given type of audio-visual stimulation to the user for a timed interval to hold him or move him to a desired state. At the end of the interval, the user state is again measured and a further timed audio-visual response according to his measured state is presented to the user.

In U.S. Pat. No. 5,596,994, an automated and interactive positive motivation system is disclosed. The system of this arrangement permits a physician, counselor or trainer to produce and send a series of motivational messages and/or questions to a client to change or reinforce a specific behavioral problem.

A drawback with the above references is that they do not provide for the profiling of an individual so as to provide for customized images which are specifically tailored for the individual so as to reduce or manage his or her stress. This is applicable when one considers that an image which may be restful for some may be stressful for others.

Conventional arrangements have a drawback in that the mechanisms for reducing stress, such as the images, are preselected by someone other than the user. The images chosen are based on the effect of the images on a large sample of subjects and are not tailored or personalized for an individual. In addition, conventional arrangements for measuring and reducing stress are often large and not very portable, therefore, these devices are not conducive to being used at work, in the home, or taken with the individual when they travel.

SUMMARY OF THE INVENTION

The present invention provides for system which includes a method and apparatus which helps an individual to manage a psychological and physiological state of that individual by utilizing images or stimuli such as sound, smell, etc. In the context of the present invention, the images can be still images, audio-visual images or video clips. The method and apparatus of the present invention can make up part of a personal biofeedback program for managing stress responses. With the method and apparatus of the present invention, it is possible to overcome the disadvantage of generalized image selection as in conventional arrangements. That is, with the method and apparatus of the present invention, rather than presenting an individual with images or stimuli on the basis of the effects these images or stimuli had on a large sample of subjects, the images or stimuli are linked to personal responses. The individual then utilizes these personal images or stimuli in a device that uses images or stimuli, or feedback controlled image or stimuli properties as a biofeedback mechanism for altering his or her psychological and physiological state, so as to manage and/or reduce, for example, the stress of the individual.

The present invention relates to a method of changing, managing, or helping that individual to manage a psychological and physiological state of that individual using images. The method comprises the steps of creating a personalized preferred image response profile for an individual by having the individual view a first set of images and choose images from the first set of images which provide a preferred response for the individual, wherein the personalized preferred image response profile defines preferred characteristics which are representative of common characteristics of the chosen images; selecting a second set of images from an image library which include characteristics that match the preferred characteristics of the personalized preferred image response profile; and displaying the selected second set of images to the individual help to manage a psychological and physiological state of the individual.

The present invention further relates to a method of changing, managing or helping an individual to manage a psychological and physiological state of that individual using images which comprises the steps of showing a first set of images to the individual; measuring a physiological state of the individual as the individual views the first set of images; and recording images from the first set of images which provide a preferred response based on the measured physiological state of the individual, so as to create a personalized preferred image response profile that defines preferred characteristics which are representative of common characteristics of the recorded preferred images.

The present invention also relates to a system which changes, manages or helps to manage a psychological and physiological state of an individual using images. The system comprises an image display device which is adapted to store a personalized preferred image response profile for an individual and to store and display a set of images from an image library; and a detector device which measures physiological characteristics of the individual, wherein the physiological characteristics are indicative of a stress level of the individual. The image display device comprises a control mechanism which selects images from the set of images that include attributes that match attributes of the personalized preferred image response profile, and displays the selected images in a desired sequence in accordance with a stress level of the individual as measured by the detection device, to control a stress level of the individual.

The present invention also relates to a method of helping an individual manage his/her psychological and physiological state, the method comprising the steps of showing a set of stimuli to the individual; measuring a physiological state of the individual as the individual views the set of stimuli, and making a recording of stimuli from the set of stimuli which provide a preferred response based on the measured physiological state of the individual, so as to create a personalized preferred response profile that defines preferred characteristics which are representative of common characteristics of the recorded stimuli.

BRIEF DESCRIPTION OF THE DRAWINGS

FIG. 6 is a chart illustrating an example of a comparison of images and attributes which can be utilized with the system of the present invention.

DETAILED DESCRIPTION OF THE INVENTION

Figure 1:
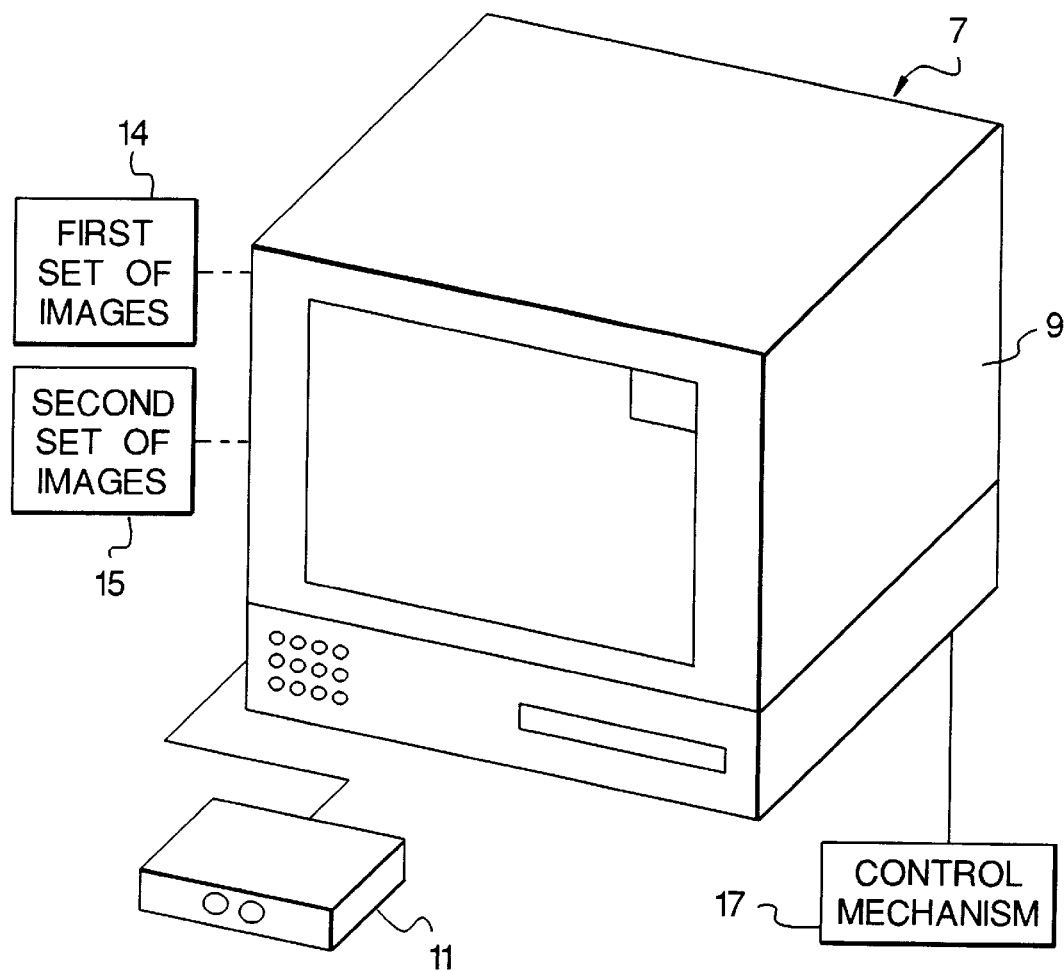
FIG. 1 illustrates a schematic view of an imager apparatus of the present invention.

Referring now to the drawings, wherein like reference numerals designate identical or corresponding parts throughout the several views, FIG. 1 illustrates a schematic view of the system of the present invention which includes a biofeedback imager apparatus 7 that can be utilized to monitor and manage a psychological and physiological state of an individual. That is, imager apparatus 7 is utilized by an individual as a stress management mechanism. Although the present invention will be primarily described in terms of using images as a component of a stress management mechanism, it is recognized that other stimuli such as sound, smell, etc. can be presented to the individual and utilized within the context of the present invention.

As illustrated in FIG. 1, imager apparatus 7 comprises an image display device 9 which can be a computer or some form of electrical imaging device such as a Photo CD player, slide projector, CD player, VCR, DVD player, TV, hand held device such as a GAME BOY, etc., which is compatible with a computer. Furthermore, image display device 9 can be correlated with a heating or vibrating assembly which can apply heat to, for example, the chair on which the individual is seated, or movement to, for example, a doll, based on the images and the measured stress of the user.

Image display device 9 can store a first set of images 14 on, for example, a disk or storage card, which are representative of a personalized preferred image response profile for an individual, the details of which will be described later. First set of images 14 can be tailored to the individual and can include a series of images based on a variety of themes (such as the ocean, a forest, a desert, a sunset, etc.) or his/her own personal images (e.g. your family). Each series may go from a chaotic state to a calm state and finally end in a placid or serene state based on the psychological and physiological state of the individual. Image display device 9 can further be adapted to store and display a second set of images 15 from an image library or from his/her own personal images, which can be stored therein by way of, for example, a disk or storage card. As previously discussed, the images can be still images, audio-visual images or video clips.

FIG. 1 further illustrates a detector device 11 which can be operationally associated with image display device 9. Detector device 11 can be a measuring or monitoring apparatus that can interact with a user's body so as to measure physiological characteristics, such as galvanic skin response, a temperature of the extremities such as the fingers, a blood pressure, a pulse rate, breathing, eye movements, or other functions of an individual that can be related to the user's psychological state and thereby the user's level of stress. Detector device 11 can be attachable to a user's body in a non-invasive manner or could be a device that does not contact the user's body such as an optical monitor which can be used to measure the pupil dilation of the user.

Image display device 9 can further include a control mechanism 17 which can comprise software to interact with detector device 11 and image display device 9, so as to display a preferred image on image display device 9 based on the measured physiological characteristics or level of stress of the individual. For example, control mechanism 17 can convert the changes in stress related physiological functions of the individual to a signal that can trigger a change in the sequence or type of images displayed by image display device 9. More specifically, control mechanism 17 can include software that is designed to select images from second set of images 15 that include attributes defined by the personalized preferred image response profile, and display the selected images in a desired sequence in accordance with the stress level of the individual as measured by detection device 11, to help manage a stress level of the individual.

The process of creating a personalized preferred image response profile for determining first set of images 14 for each individual will now be described. The personalized preferred image response profile is created by having an individual look at a wide variety of images and measuring the effects of the images on the individual's psychological state as indicated by their physiological state. The measurements can be made by recording the person's EMG, EEG, galvanic skin response, skin temperature, heart rate, blood pressure, eye movement such as pupil dilation or any measurable indication of stress. The measurements are matched to the image the individual was viewing at the time and show how the individual reacts to a specific image or set of images. From this data, a personalized preferred image response profile is created for each individual. First set of images 14 will generally be those images which provide a preferred response, such as a lowering of a stress level of the individual. Therefore, the personalized preferred image response profile can include data from first set of images 14 which is representative of common characteristics, or attributes of the first set of images which tend to provide a preferred response to the individual. The personalized preferred image response profile can then be used to select images from an image library which includes second set of images 15. The selected images can be used by the individual as their personal biofeedback images, and thus, by using the personalized preferred image response profile, images are selected that have a desired effect for the individual. More generally, the personalized preferred image response profile may be comprised of a set of information that describes the selected images and others that match the response profile.

As an example, to use his or her personalized preferred image response profile, the individual accesses an image library (for example, via the Internet or interactive CD-ROM), and keys in a number that links to their personalized preferred image response profile via a code. The individual's personalized preferred image response profile is then used by the image library to select images from the image library. Thumb nails (small low resolution images) of these selected images can be shown to the individual so that the individual can chose from the selected images, the images he or she wants and the order of the images, before the images are downloaded or sent to the individual for use as biofeedback in their personal biofeedback imager (i.e. a FLASH PIX format). The personalized image response profile allows the user to pick from a variety of categories such as seascapes, desert scenes, forest scenes or his or her own personal images such as from his or her house, garden or favorite museum to name a few examples. This allows the user to change the images that are used as biofeedback without the risk of the images having an adverse effect on the individual's mental state.

Once the individual has established his or her personalized preferred image response profile, the user interacts with detecting device 11, and loads his/her selected images (from second set of images 15) into the imaging device. The output from detecting device 11 feeds into control mechanism 17 which is connected to image display device 9. These connections can be via a wire or remote. The user can set a base state by recording the levels of his or her stress related functions such as EMG, EEG, galvanic skin response, skin temperature, heart rate, blood pressure, eye movement. etc. An image from the selected images of second set of images 15 which relates to his or her level of stress is displayed on image display device 9; at this point, he or she begins his or her stress reduction regime and his or her changing level of stress is manifested as the images change in transition. For example, as his or her stress level decreases, the images could change from a chaotic state to a serene state. In another form, the images may change from one image to another unlike image while still showing the changing level of the individual's stress on the basis of the individual's personalized preferred image response profile. The images may be based on resolution, color, contrast, content, etc.

The individual's personalized preferred image response profile may also be used to choose images and return them to the individual as single prints, or a set of prints to be hung on walls. Another technique which may be used to present a sequence of images to the individual could be the use of a sheet of lenticular material placed over the surface of a number of interleaved images. Depending upon the viewing angle, the individual will see only one of a number of images behind the lenticular surface. As the angle of view changes, other images will become visible, one at a time. The individual would be able to review his sequence of calming images by merely changing the viewing angle by hand, (see for example U.S. Pat. Nos. 5,543,964 and 5,639,580, as well as co-pending U.S. application Ser. No. 08/882,903 the subject matter of which is herein incorporated by reference).

Referring now to examples of the system of the present invention, FIGS. 2–4 and 7 illustrate flow charts representative of the application of the invention based on an individual's visit to a retailer, establishing remote communication such as going on-line via, i.e. the Internet, or visiting a medical practitioner. Each of the illustrated flow charts can be in the form of software manipulated by the individual or medical practitioner, or a questionnaire completed by the individual. As noted in FIG. 2, in applying the system of the present invention, the individual can go to a retailer or establish a remote communication such as going on-line (step 100). At step 200, it is determined whether the individual has a personalized preferred image response profile. If the answer at step 200 is no, an instruction is given to create a personalized preferred image response profile for the individual (step 300) using a personalized preferred image response profile kit.

Figure 3:
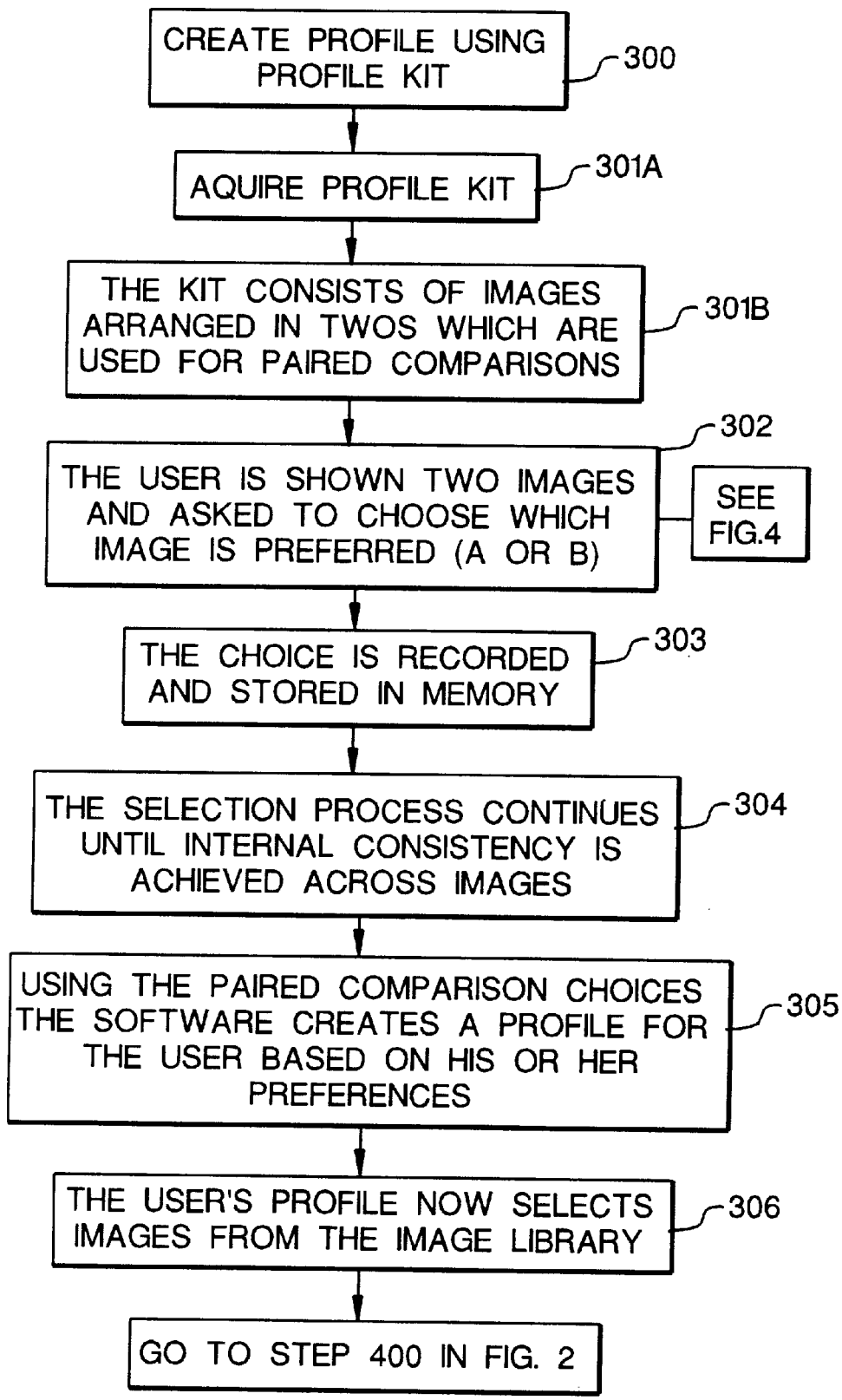
FIG. 3 is a flow chart representative of the system of the present invention.
Figure 4:
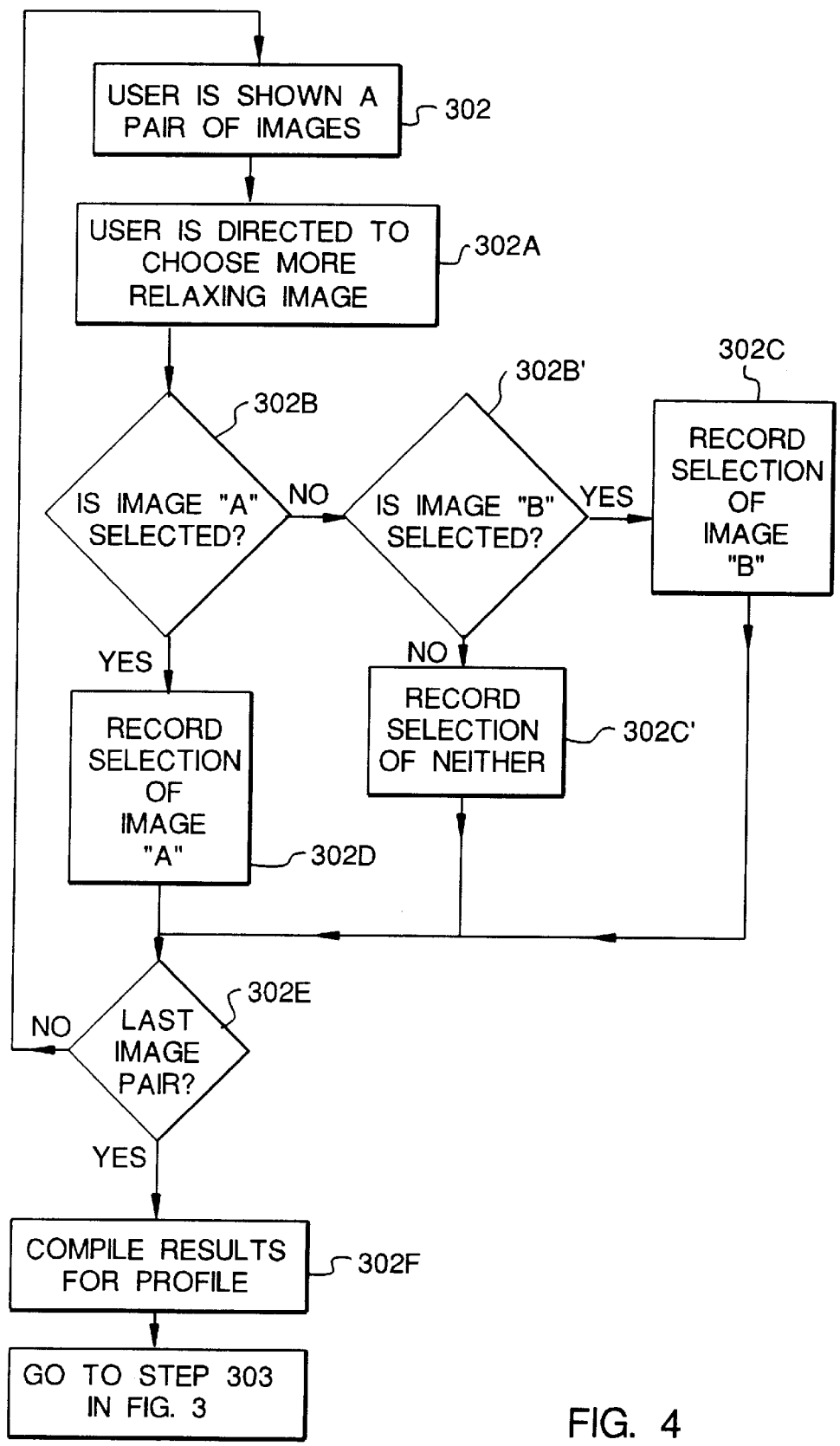
FIG. 4 is a further flow chart showing a comparison of images which can be utilized within the system of the present invention.
Figure 5:
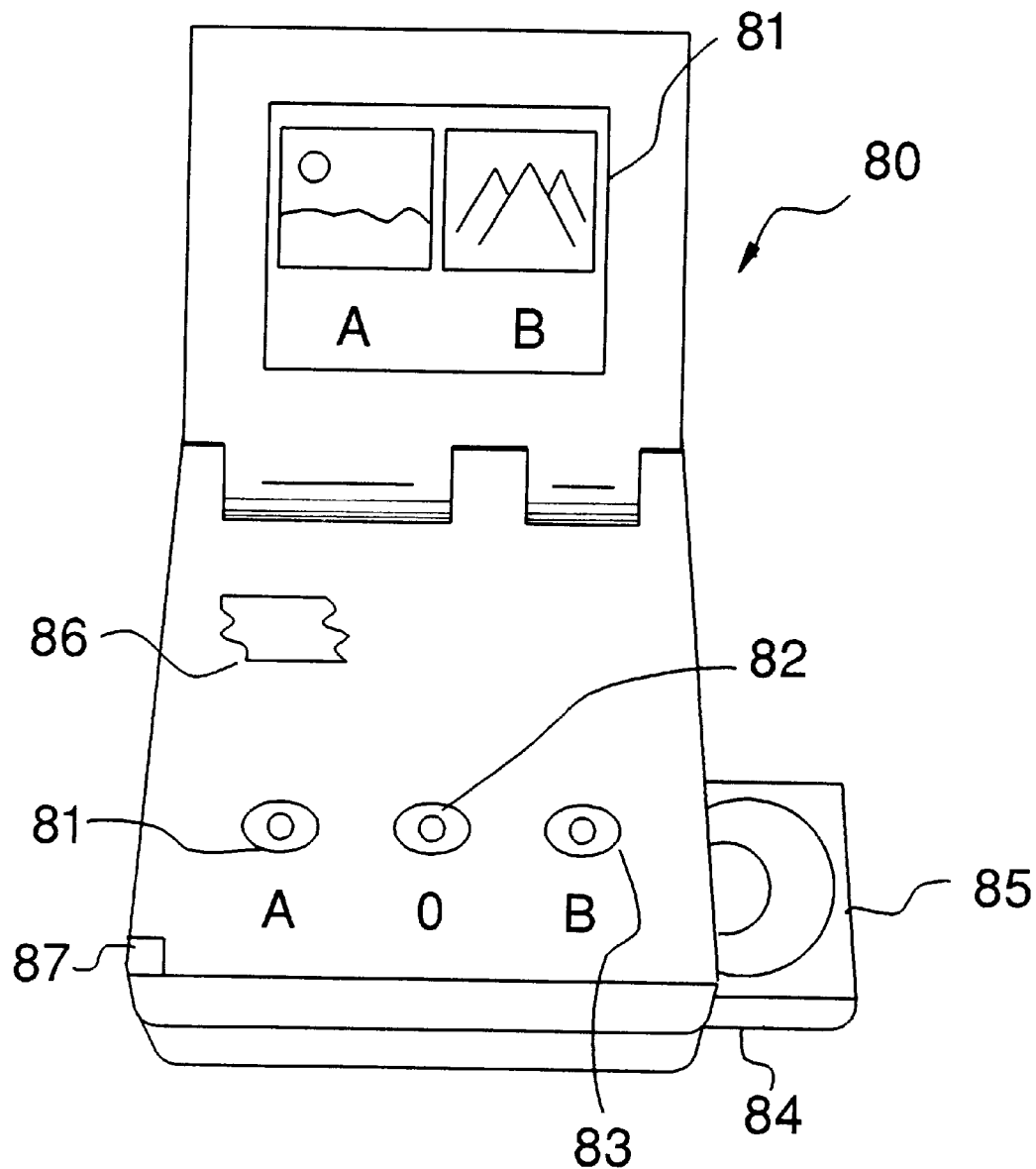
FIG. 5 is an example of a selector device which can be used for paired comparisons of images.

Referring now to FIG. 3, the process of creating a personalized preferred image response profile will now be explained. As illustrated in FIG. 3, the individual obtains a profile kit (step 301A) and as illustrated in step 301B, the profile kit can include images arranged in twos which are used for paired comparisons. The user is then shown two images and asked to chose which image is preferred (step 302). FIG. 4 illustrates a flow chart with respect to the comparison of images of step 302, while FIG. 5 illustrates a selector device 80 of the system of the present invention, which can be used by the individual to view, compare and choose images. As shown in FIG. 5, selector device 80 includes a viewing screen 81 which can display images A and B and selector buttons, switches, etc. 81, 82 and 83. Selector button 81 corresponds to image A and is activated or depressed by the individual when image A provides a preferred response when compared to image B; selector button 83 corresponds to image B and is activated or depressed by the individual when image B provides the preferred response when compared to image A, and selector button 82 can be activated or depressed by the individual when no image is preferred. Selector device 80 can include a CD player 84 which permits the images to be loaded via a CD 85. Selector device 80 can further include a control logic memory module 87 which records and stores the individual's selections, as well as a ticket printing section 86 which can print out the individual's selections.

As noted in FIG. 4 and using selector device 80 as illustrated in FIG. 5, after the individual is shown a pair of images (step 302), the user is then directed to chose the more relaxing image (step 302A). In step 302A, the user can provide a direct response with respect to the preferred images by activating or pressing one of selector buttons 81–83 of selector device 80. As an alternative, preferred images can be automatically chosen based on a measured physiological state of the individual by interacting a detecting device 11 as illustrated in FIG. 1 with selector device 80 of FIG. 5.

After step 302A, there is a check to see if an image "A" is selected (step 302B). If the answer to step 302B is no, there is a check to see if image "B" is selected (step 302B'). If the answer to step 302B' is yes, the selection of image "B" is recorded (step 302C). If the answer to step 302B' is no, then there is a recording that neither image has been selected (step 302C'). If the answer to step 302B is yes, there is a recording of the selection of image "A" (step 302D). After either of steps 302C, 302C' or 302D, there is a check to see if the image pair shown to the individual is the last image pair (step 302E). If the answer to step 302E is no, then above steps are continued as noted in the flow chart of FIG. 4 until the last image pair is chosen and the complete selection of images is noted by the individual. After step 302E, the process proceeds to compile the results of the images chosen by the individual (step 302F).

Referring back to FIG. 3, the chosen images or choices are thereafter recorded and stored in memory (step 303). At this point, the selection process could be continued until internal consistencies are achieved across images (step 304). For example, and with reference to FIG. 6, each of the images in the profile kit can include certain attributes or characteristics. FIG. 6 shows a chart of images versus attributes. In viewing the images selected by the individual, there could be a check as to which are the dominant attributes or characteristics of the selected images, and these attributes or characteristics can be utilized to help create the personalized preferred image response profile of the user. Also, a search can be initiated using these attributes or characteristics as described in, for example, co-pending application U.S. Ser. No. 08/998,106, the subject matter of which is herein incorporated by reference. In step 305, the selection results of the paired comparisons as well as the review of the attributes of the chosen images or the sequence of the images provides the bases for the creation of a personalized preferred image response profile for the user based on his or her preferences. The user's individual personalized preferred image response profile can now be utilized to select a second set of images 15 from an image library as noted in step 306 or from his/her own personal images. Thereafter, the process goes to step 400 of FIG. 2 where the individual can use an imager apparatus 7 as illustrated in FIG. 1 and an image library including second set of images 15 can be requested.

In step 500, images from second set of images 15 using the personalized preferred image response profile are selected and viewed in categories (step 600). Thereafter, an individual can select image categories (step 700), view the images (step 800), select images (step 900) based on the personalized preferred image response profile, and arrange the images in a desired sequence for achieving stress reduction (step 1000). As a further option, a computer program can be utilized to update the user's profile using data from the newly selected images (step 1010) and the media for showing the images can be selected (step 1020).

Figure 2B:
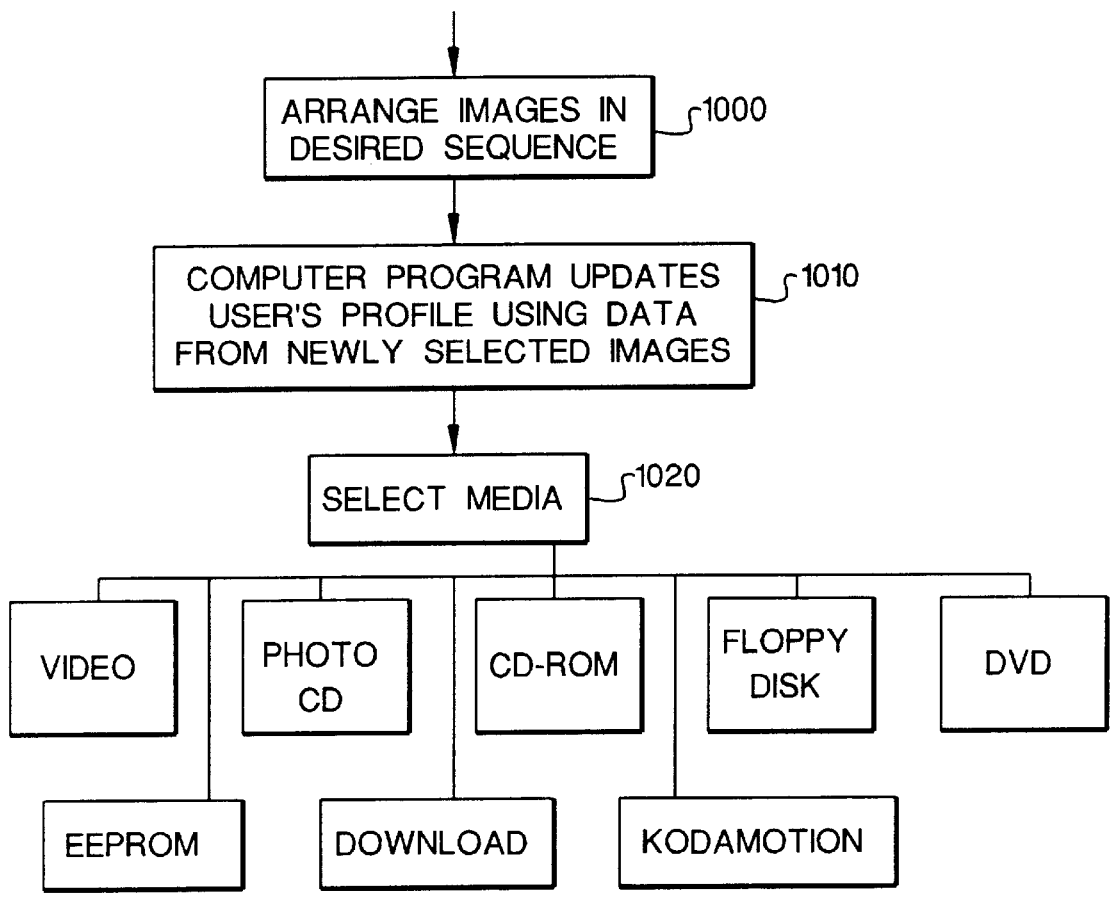
FIG. 2 is a flowchart illustrating a system of the present invention for managing stress.

As illustrated in FIG. 2, the media for showing the images can be in the form of a video, photo CDs, CD ROMs, floppy disks, DVD, lenticular imaging, downloaded or EEPROM.

Therefore, with the process of the present invention, the individual creates a personalized preferred image response profile by viewing a first set of images such as from a profile kit that includes images arranged in pairs, and compares and chooses images from the first set of images which provide a preferred response for the individual. In making the comparison choices between images as illustrated in the flow charts of FIGS. 3 and 4, those images which provide a preferred stress response level for the individual are chosen or automatically selected based on the individual's measured present stress level. The selected images from this comparison are utilized to create a profile for the user based on his or her preferences. Thus, the personalized preferred image response profile will define preferred characteristics which can be representative of common characteristics of the chosen images. The individual can then select a second set of images from an image library which includes characteristics that match the preferred characteristics of the personalized preferred image response profile.

Having created the personalized preferred image response profile, which can be recorded on, for example, a disk, an imager apparatus 7 including detector device 11 as illustrated in FIG. 1 can be used to measure the individual's present stress level. Based on the individual's personalized preferred image response profile, imaging device 9 can display selected images from the image library to the individual in a sequence chosen by the individual, in accordance with the measured stress level of the individual, to enable the individual to manage and/or lower his or her stress level.

Figure 7:
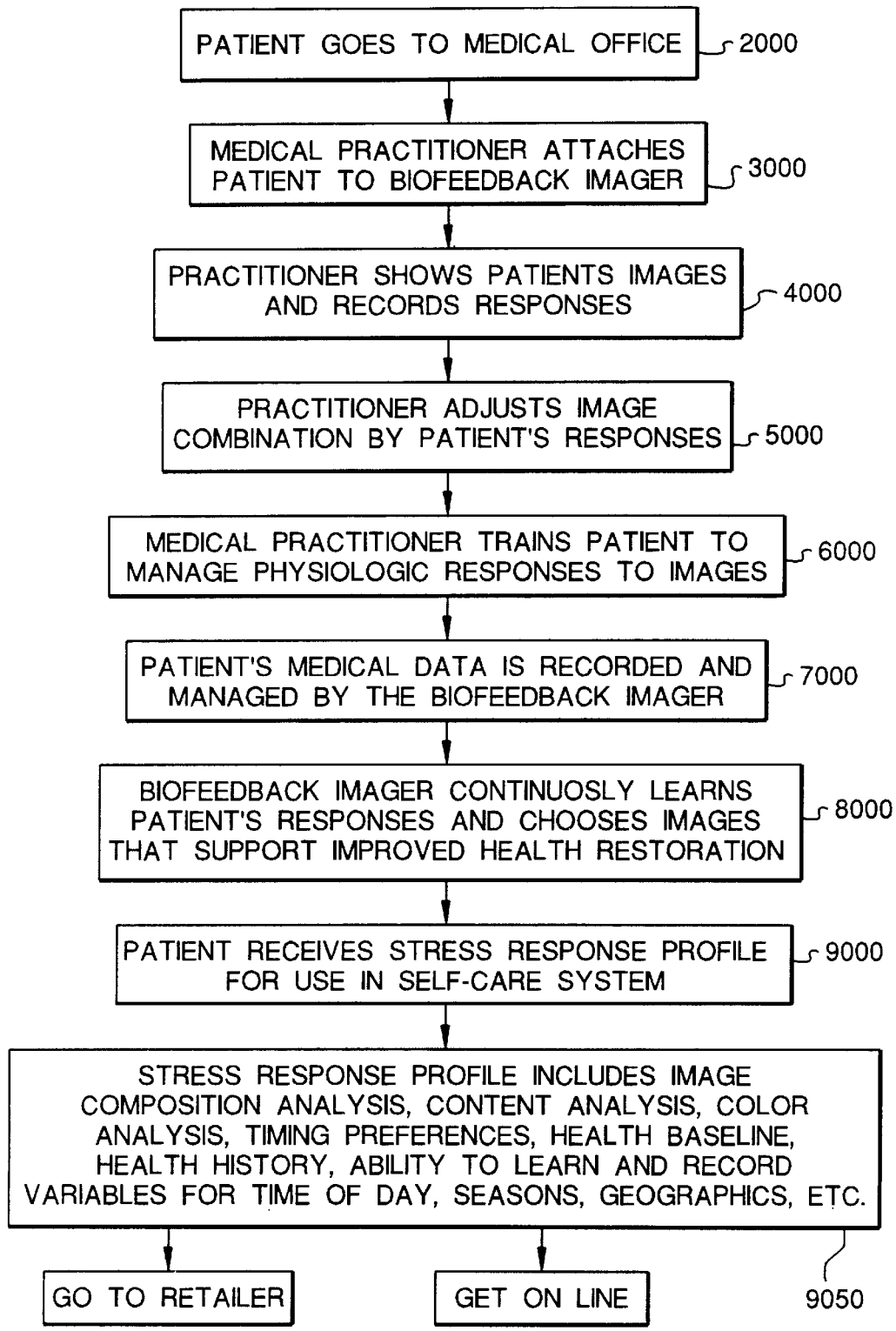
FIG. 7 is a flow chart of an alternative system of the present invention.

In a further feature of the present invention and as shown by the flow chart of FIG. 7, an individual can visit a medical office (step 2000) to control stress in accordance with the present invention. As illustrated in FIG. 7, in a medical office, a medical practitioner attaches the patient to imager apparatus 7 (step 3000) as shown in FIG. 1, displays images to the patient and records responses to these images (step 4000). It is noted that imager apparatus is further capable of interfacing with existing biofeedback equipment. Thereafter, the practitioner or software adjusts the image combination in view of the patient's responses (step 5000) and the practitioner trains the patient to manage his physiological responses to images (step 6000). The patient's medical data is then recorded and managed by imager apparatus 7 (step 7000), and imager apparatus 7 continuously learns the patient's responses, builds the personalized preferred image response profile and chooses images that support improved health restoration (step 8000). The patient can thereafter receive a personalized preferred image response profile for use in a self-care system (step 9000).

The personalized preferred image response profile can include image composition analysis which, for example, analyzes images based on the attributes shown in FIG. 6. The stress response profile can also include color analysis, timing preference, health baseline, health history, ability to learn and record variables for time of day, seasons, geographies, personal or family images, etc. (step 9050). Having the personalized preferred image response profile created by a medical practitioner, the individual can now go to a retailer or a remote connection (i.e. on-line) as illustrated in FIG. 7 and described in the flow chart of FIG. 2, to obtain images which help manage stress.

Therefore, the method and apparatus of the present invention overcomes the disadvantage of generalized image selection. Rather than presenting the individual with images chosen on the bases of the effects these images had on a large sample of subjects, the images are linked to personal responses. The individual uses the personalized images in a device that uses images or feedback controlled image properties as a biofeedback mechanism for altering his or her psychological state for the better. It is recognized that in addition to managing stress, the method and apparatus can also be used as a tool to motivate, teach, focus, visualize, etc.

The method and apparatus also permits the use of the individual's personalized preferred image response profile as a way of allowing the individual to chose images or sets of images from a number of different categories of images such as seascapes, desert scenes, forest scenes, etc. A provision could also be made to include the individual's own personal images (e.g. your family) in the personalized preferred image response profile.

The personalized preferred image response profile can also be used as a way of preventing the individual from having to choose images or sets of images from a large library of images. The images are selected by comparing the attributes of the images to the personalized preferred image response profile.

The method and apparatus of the present invention also permits an individual to use the personalized preferred image response profile to sort, compare, select and keep track of images. With the method and apparatus of the present invention, it is also possible to generate a chart or record of stress levels for periods of time which can be shared with, for example, physicians.

The method and apparatus of the present invention also provides for a device which can be utilized to manage stress and at the same time is portable enough so that it can be used at home, at work or during traveling.

Also, although primarily described in terms of images, the present invention is not limited to the use of images in creating a personalized preferred response profile and helping individuals manage stress. As previously discussed, stimuli such as sound, smell, etc., which provide a preferred response can also be used, alone or with images, as a basis for creating the personalized preferred response profile and helping individuals manage their stress.

The invention has been described in detail with particular reference to certain preferred embodiments thereof, but it will be understood that variations and modifications can be effected within the spirit and scope of the invention.

What is claimed is:

1. A method of managing a psychological and physiological state of an individual using images, the method comprising the steps of:

creating a personalized preferred image response profile for an individual by having the individual view a first set of images and choosing image from the first set of images which provide a preferred response for the individual, wherein said personalized preferred image response profile defines preferred characteristics which are representative of common characteristics of the chosen images;

selecting a second set of images from an image library which include characteristics that match the preferred characteristics of the personalized preferred image response profile; and displaying the selected second set of images to the individual to manage a psychological and physiological state of the individual.

2. A method according to claim 1, comprising the further step of measuring a physiological state of the individual, wherein said step of displaying the selected second set of images to the individual comprises displaying the selected second set of images in a desired sequence in accordance with the measured physiological state of the individual.

3. A method according to claim 1, wherein said step of creating the personalized preferred image response profile comprises the step of:

arranging the first set of images in pairs of images; and showing the pairs of images to the individual to permit the individual to compare the pair of images;

wherein said chosen images from the first set of images are preferred images for each pair of images, which provide the preferred response for the individual.

4. A method according to claim 2, wherein the physiological state of the individual is measured by recording at least one of an EMG, EEG, galvanic skin response, skin temperature, heart rate, blood pressure, eye movement or pupil size of the individual as the individual views the images.

5. A method according to claim 1, comprising the further step of placing the selected second set of images on a desired output format.

6. A method according to claim 1, comprising the further step of storing the first and second set of images at a remote location.

7. A method of managing a psychological and physiological state of an individual using images, the method comprising the steps of:

showing a first set of images to the individual;

measuring a physiological state of the individual as the individual views the first set of images; and recording images from said first set of images which provide a preferred response based on the measured physiological state of the individual, and creating a personalized preferred image response profile that defines preferred characteristics which are representative of common characteristics of the recorded preferred images.

8. A method according to claim 7, comprising the further steps of:

selecting a second set of images from an image library which include characteristics that match the preferred characteristics of the personalized preferred image response profile; and displaying the selected second set of images to the individual to manage the psychological state of the individual.

9. A method according to claim 7, comprising the further steps of:

selecting a second set of images from the individual's own personal images; and displaying the selected second set of images to the individual to manage the psychological state of the individual.

10. A method according to claim 7, wherein the physiological state of the individual is measured by recording at least one of an EMG, EEG, galvanic skin response, skin temperature, heart rate, blood pressure, eye movement or pupil size of the individual as the individual views the images.

11. A method according to claim 8, comprising the further step of placing the selected second set of images on a desired output format.

12. A method according to claim 8, comprising the further step of storing the first and second set of images at a remote location.

13. A system which manages a psychological and physiological state of an individual using images, the system comprising:

an image display device which is adapted to store a personalized preferred image response profile of an individual, and to store and display a set of images from an image library; and a detector device which measures physiological characteristics of the individual, wherein said physiological characteristics are indicative of a stress level of the individual;

said image display device comprising a control mechanism which selects images from said set of images that include attributes that match attributes of the personalized preferred image response profile, and displays the selected images in a desired sequence in accordance with a stress level of the individual as measured by said detector device, to manage a stress level of the individual.

14. A system according to claim 13, further comprising a selector device which includes a viewing screen which displays a further set of images in pairs and selector switches which enable an individual viewing the pairs of images to select a preferred image from the pair, such that said personalized preferred image response profile is based on the selected preferred image from the pair.

15. A system according to claim 14, wherein said selector device further includes a memory module for storing the selected images.

16. A method of helping an individual manage his/her psychological and physiological state, the method comprising the steps of:

showing a set of stimuli to the individual;

measuring a physiological state of the individual as the individual views the set of stimuli; and making a recording of stimuli from said set of stimuli which provide a preferred response based on the measured physiological state of the individual, and creating a personalized preferred response profile that defines preferred characteristics which are representative of common characteristics of the recorded stimuli.

17. A method of managing a psychological and/or physiological state of an individual using images, the method comprising:

showing a first set of images to the individual;

choosing images from said first set of images which provide a preferred response for said individual, wherein said chosen images have common characteristics which define a personalized preferred image response profile for said individual; and recording said chosen images and/or said personalized preferred image response profile for said individual.

* * * * *